United States Patent
Joyce et al.

(10) Patent No.: US 7,757,567 B2
(45) Date of Patent: *Jul. 20, 2010

(54) DISPENSING MEASUREMENT DEVICE AND METHOD OF MEASURING DISPENSING

(75) Inventors: Jonathan Livingston Joyce, Independence, KY (US); Kelly Stewart Teegarden, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 367 days.

This patent is subject to a terminal disclaimer.

(21) Appl. No.: 12/004,857

(22) Filed: Dec. 21, 2007

(65) Prior Publication Data

US 2008/0149663 A1 Jun. 26, 2008

Related U.S. Application Data

(60) Provisional application No. 60/876,242, filed on Dec. 21, 2006.

(51) Int. Cl.
*G01F 1/56* (2006.01)
(52) U.S. Cl. .................................... 73/861.08
(58) Field of Classification Search ............... 73/149, 73/195, 239, 861, 861.08, 861.13
See application file for complete search history.

(56) References Cited

U.S. PATENT DOCUMENTS

| | | | |
|---|---|---|---|
| 4,741,981 A | 5/1988 | Hashimoto et al. | |
| 4,891,993 A | 1/1990 | Barker | |
| 4,934,566 A | 6/1990 | Guerette | |
| 5,383,373 A | 1/1995 | Knowles, Jr. et al. | |
| 5,423,454 A | 6/1995 | Lippman et al. | |
| 5,435,909 A | 7/1995 | Burrows | |
| 5,878,381 A | 3/1999 | Gemmell et al. | |
| 6,360,181 B1 | 3/2002 | Gemmell et al. | |
| 2003/0089733 A1 | 5/2003 | Cain et al. | |
| 2005/0252930 A1 | 11/2005 | Contadini et al. | |
| 2008/0149663 A1 | 6/2008 | Joyce et al. | |
| 2009/0158836 A1* | 6/2009 | Joyce et al. | 73/149 |

FOREIGN PATENT DOCUMENTS

| | | |
|---|---|---|
| GB | 2 087 839 A | 6/1982 |
| JP | 09 079890 A | 3/1997 |
| JP | 9 244 289 A | 9/1997 |

OTHER PUBLICATIONS

PCT International Search Report Dated Dec. 21, 2007—4 pgs.

* cited by examiner

*Primary Examiner*—John Fitzgerald
(74) *Attorney, Agent, or Firm*—Larry L. Huston; Leonard W. Lewis; Steven W. Miller

(57) ABSTRACT

A dispensing measuring device. The device correlates the relative proximity between a Hall effect sensor and a magnet. One is held stationary, while the other is movable in response to ordinary actuation which occurs during dispensing. Detection of changes in the proximity are correlated to the amount of material dispensed.

12 Claims, 2 Drawing Sheets

US 7,757,567 B2

DISPENSING MEASUREMENT DEVICE AND METHOD OF MEASURING DISPENSING

CROSS REFERENCE TO RELATED APPLICATION

This application claims the benefit of the filing date of U.S. Patent Application No. 60/876,242 filed Dec. 21, 2006.

FIELD OF THE INVENTION

The present invention relates to measuring materials being dispensed and more particularly to measurements which may not be detectable by the user.

BACKGROUND OF THE INVENTION

Measurements of materials being dispensed is known in the art. For example, magnets and Hall effect sensors have been used to indicate qualitative dispensing. Also, medication compliance monitoring is shown in US 2003/0089733 A1, dispensing of a predetermined volume of liquid is shown in GB2087839 A, U.S. Pat. No. 4,934,566 shows portion monitoring based upon a slidable control stem, and U.S. Pat. No. 6,360,181 B1 shows toilet tissue usage data collection. Generally, these references rely upon the proximity of the Hall effect sensor and magnet to indicate a change in state or in component operating position. Such a change is then related to the amount of material dispensed.

However, none of these attempts deals with the problems which occur when the amount of material being dispensed changes as a function of time and usage of that dispenser. For example, a pressurized container, such as one containing propellant dispensed air freshener, will dispense less material as depletion of the propellant occurs, due to less pressurization of the material to be subsequently dispensed. Further, a long continuous burst of dispensing will release a different amount of product than several quick bursts having the same cumulative dispensing time. The amount to be dispensed is indeterminate, i.e. a user may dispense an unknown or a desired quantity one time, and a non-integer multiple of that quantity with the next usage. This makes measuring more complex, than when the does occur in discrete units, such as sheets of toilet tissue or predetermined volumes of liquid.

Additionally, when using a pump-type dispenser, such as a squeeze trigger 23 liquid fabric refresher, partial pulls of the trigger 23 will typically result in only partial dispensing of the pump charge. This causes less material to be dispensed, dependent upon the trigger 23 stroke. When using an aerosol dispenser, depletion of the propellant over time will affect dispensing.

However, accurate measurement of material to be dispensed requires the factors be considered. Furthermore, the measurement should occur in a matter not readily detectable to the user or which does not interfere with normal usage patterns.

SUMMARY OF THE INVENTION

In one embodiment the invention comprises a device for quantitatively measuring an amount of a material dispensed. The device comprises a reservoir for holding a material therein, a dispensing orifice for dispensing material contained in said reservoir, and a dispenser for dispensing the material from the reservoir through said orifice. The dispenser has an actuator movable relative to said reservoir and a member which is stationary relative to said dispenser. A Hall effect sensor is disposed on one of said dispenser and said stationary member, and a magnet is disposed on the other of said dispenser and said stationary member, whereby relative movement between said magnet and said Hall effect sensor produces a signal in response to said movement. The signal is correlatable to a quantity of material dispensed from said reservoir. The signal may be correlatable to the quantity of material being dispensed from the reservoir throughout dispensing of substantially all of the material contained in the reservoir.

All patents and patent applications cited herein are incorporated herein by reference.

DETAILED DESCRIPTION OF THE INVENTION

The device comprises a reservoir for holding a material therein. The reservoir may be fluid tight, if the material to be dispensed is a gas, liquid or is mixed with a gaseous propellant. The reservoir may be mounted in any desired relationship with respect to a dispensing orifice for dispensing the material to its desired end use.

The device further has a dispenser for dispensing the material from the reservoir through the orifice. Various types of dispensers are known, such as threaded screw drives for advancing a piston as occurs with many anti-perspirants, a pump as occurs with many cleaners, a pressure release valve as occurs with many air fresheners and shaving creams, a lid which opens to allow manual access to and retrieval the product as occurs with wet wipes, a flexible squeeze package as occurs with toothpaste tubes, a resealingly openable bag as occurs with food storage, a walled container having a slider to open/close a lid as occurs with food storage; etc. Suitable dispensers may be made according to the teachings of commonly assigned U.S. Pat. Nos. 4,122,978; 5,000,356; 4,865,231; Des. 393,999; 6,139,185; 6,149,304; 6,164,821; 6,325,239 B2; 6,394,299 B1; 6,722,520 B2 and 6,981,658 B2.

Figure 1:
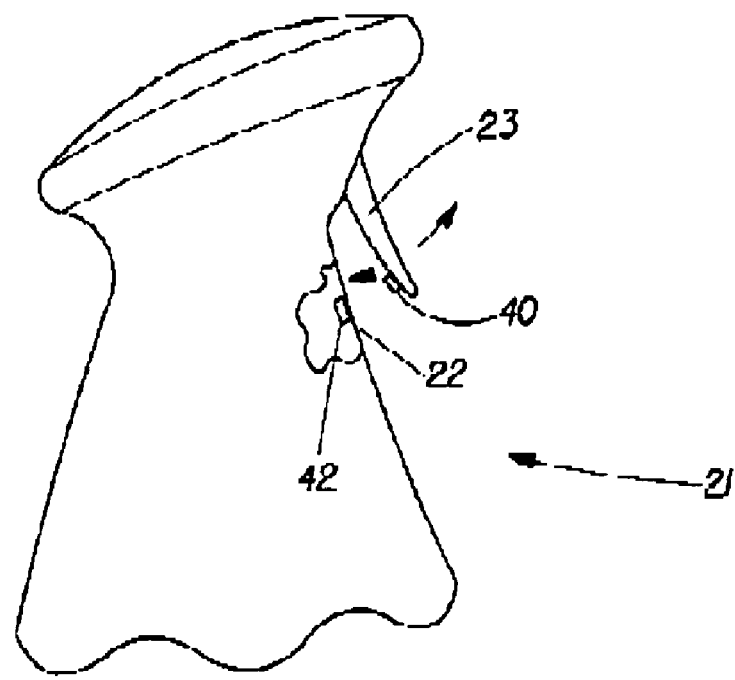
FIG. 1 is a fragmentary side view of a trigger actuated dispenser according to the present invention, shown partially in cutaway.

Referring to FIG. 1, a first embodiment of the invention comprises a method and device 21 for measuring propellant dispensed sprays or trigger pump sprays. Exemplary sprays include insecticides, perfumes, paints, cleansers, topical medicaments, anti-perspirants, hair sprays, room air fresheners, etc. The specific example below will be described with reference to Febreze Air Effects air freshener, although one of skill will recognize the invention is not so limited.

The dispenser may have an actuator movable relative to the reservoir or other portions of the device 21 and a member 22 which is stationary relative to the movable actuator. The movable actuator may be a trigger 23 which functions as or activates a pump, a dial 33 which advances a piston along a screw thread, a lid which opens by pivoting about hinges, or a trigger 23 or button which functions to open a pressure release valve, as illustrated, etc.

A Hall effect sensor 40 may be disposed on one of the movable actuator or stationary member 22. The Hall effect sensor 40 measures voltage on the opposite sides of a sheet of conducting or semiconducting material in the form of a Hall element, also referred to as a van der Pauw element. An electric current flows through the Hall effect sensor 40. The electric current is created by a magnetic field applied perpendicular to the Hall effect sensor 40.

The magnet 42 may be disposed on the other of the movable actuator and stationary member 22, whereby relative movement between the magnet 42 and Hall effect sensor 40 produces a signal in response to movement of the movable actuator. While either the magnet 42 or Hall effect sensor 40 can be mounted on either component, as noted above, it may be desirable to mount the magnet 42 on the moving actuator and the Hall effect sensor 40 on the stationary member 22. This allows the wires 44 connecting the Hall effect sensor 40 to be held in position without significant movement and potentially becoming loose. For many geometries, this configuration also makes it easier to prevent the use of the measuring device 21 from interfering with the normal product usage and corrupting the data.

Figure 4:
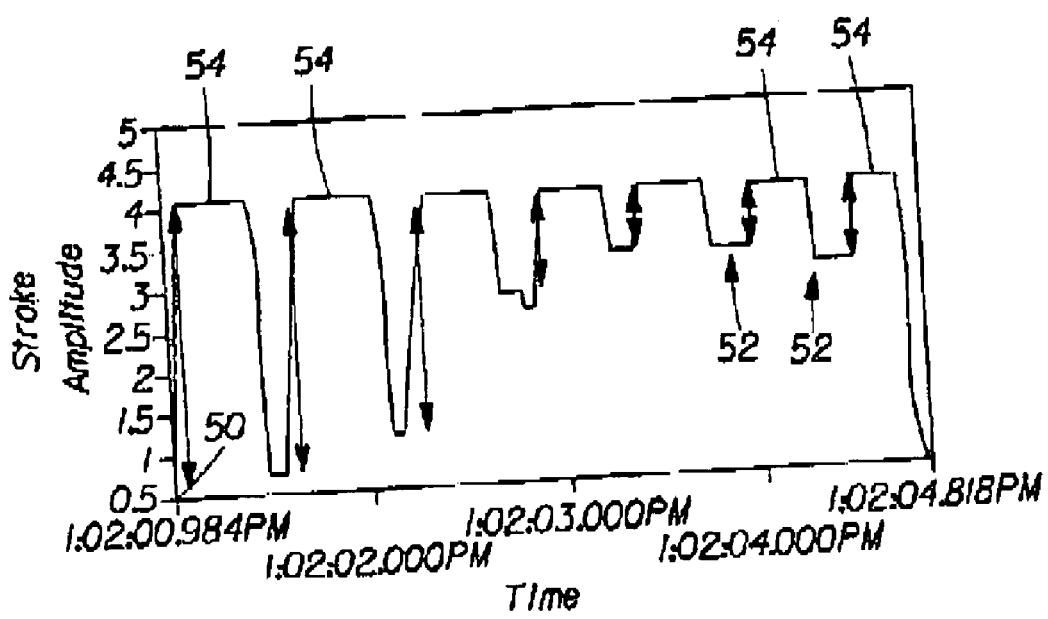
FIG. 4 is a performance curve showing the relationship between trigger displacement and dispensed material for a commercially available aerosol product, showing time on the abscissa and stroke amplitude on the ordinate for seven dispensing cycles.

Referring to FIG. 4, seven dispensing cycles are shown. The first three cycles illustrate relatively complete strokes, while the last four cycles indicate partial strokes occurred. The first stroke went from an initial trigger position 50, to a final trigger position 54. The partial strokes went from an intermediate trigger position 52 to the final trigger position 54. The stroke amplitude and position relative to the trigger 23 motion is indicated by the vertical lines with double arrowheads.

The resulting signal produced by the Hall effect sensor 40 is typically correlatable to a quantity of material dispensed from the reservoir and precise. The signal may be correlatable to the quantity of material being dispensed from the reservoir throughout dispensing of substantially all of the material contained in the reservoir, or throughout only the first portion, last portion or any intermediate portion of the material being dispensed. The signal from the Hall effect sensor 40 is related to the quantity, as measured in mass, of material dispensed through a functional relationship. The mass of material dispensed may be converted to volume, using the material density, if desired.

The functional relationship may be transmitted as a carrier wave, and electronically stored as in any digital or analogue media device, such as but not limited to a hard drive, flash drive, magnetic storage unit, etc. This arrangement provides the advantage that the electronically stored functional relationship may be maintained remote from the device 21, and not interfere with normal usage or adversely affect the measurement.

The functional relationship may be empirically developed, developed through computer modeling, etc. The device 21 may be set up, as described above to record the output in volts from the Hall effect sensor 40. The output may be recorded in any convenient format, such as a spreadsheet, as is well known in the art. The material is dispensed and the reservoir weighed after each dispensing incident. The dispensing may include both full and partial actuations of the actuator. For example, in a trigger 23 type dispenser, the measurements may account for both full and partial pulls of the trigger 23.

The output may be recorded as a function of the resulting weight. A functional relationship may be interpolated from the discrete data points of each dispensing cycle. The relationship may be developed by noting the starting point of the actuator, the ending point of the actuator during a dispensing cycle, then subtracting. The two positions to yield a stroke. It is to be noted that the amount of material dispensed for a particular magnitude of partial stroke may depend not only on the magnitude of the stroke, but also upon the position of the trigger 23 stroke where that stroke of any magnitude occurs. A partial stroke in one position may cause spritzing, whereas a partial stroke of the same magnitude in a different position may yield a nearly full dose.

Of course, one of skill will recognize the functional relationship may be maintained as a curve, as a lookup table, etc. The functional relationship may be output in graphical or visible form or may be maintained on computer and not seen by the user.

This procedure allows for the functional relationship to be maintained remote from the measuring device 21. Remote maintenance allows the device 21 to be used in its normal fashion, and the data downloaded later. Such subsequent downloading may allow the functional relationship to be incorporated and the dispensing measurements to be determined at such later time as may be convenient for the user.

In operation, as one dispenses material under the pressure differential provided by the propellant, there multiple pulls on the trigger 23 occur. The trigger 23 pulls may be from the fully closed position to the fully open position, from the fully closed position to a partially open position, from a partially open position to the fully open position, from the fully open position to a partially open position, from a partially open position to a fully closed position and various combinations thereof.

The full or partial strokes between the various positions may be recorded and thereby correlated to the amount of material dispensed through the functional relationship. Additionally, the duration, time and/or date of the Hall effect actuation responsive to the trigger 23 pull may be recorded or downloaded for later analysis.

Referring back to FIG. 1, the invention may be used with a trigger 23 pump sprayer. Such a sprayer may have a pump actuated in known fashion by the trigger 23. The functional relationship may be derived to yield the amount of material dispensed from the reservoir in response to various full or partial pulls of the trigger 23, for a particular fill level of the reservoir.

Figure 2:
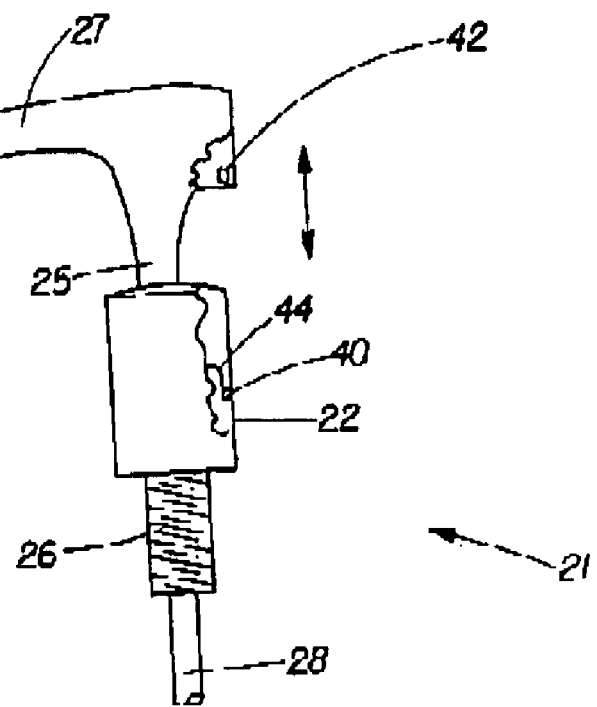
FIG. 2 is a fragmentary side view of a spring-loaded plunger, suitable for dispensing lotion, shown partially in cutaway.

FIG. 2 discloses a pump type dispenser usable for lotions, creams and relatively viscous materials. Such a dispenser has a movable plunger 25 type pump. The user depresses the plunger 25 to draw the material to be dispensed from the reservoir into a dip tube 28. A spring 26 may return the plunger 25 to the upward position, to start the next dispensing cycle. A nozzle 27 may be disposed on top of the plunger 25 to provide comfortable ergonomics for the user's hand and also to provide an orifice for dispensing of the material. The plunger 25 moves up and down relative to a stationary portion 22 of the device 21 body.

One of skill will recognize the plunger 25 may also move horizontally, or in any direction between the horizontal and vertical axes. The plunger 25 arrangement provides the advantage of rectilinear movement, easily correlatable with the functional relationship.

A Hall effect sensor 40 may be placed on either of the movable plunger 25 or the stationary portion 22 of the device 21. A magnet 42 may be placed on the other component. The relative motion therebetween as the plunger 25 is activated creates the magnetic field correlated to the material discharged and dispensed.

If desired, a tilt sensor may also be incorporated into the device 21. The tilt sensor may be used to determine if the reservoir was tipped off-center during dispensing. If so, less material may be dispensed from the reservoir and the results may not tally with the functional relationship, as expected. For example, upon tilting at the end of a dip tube 28, if present, may not be immersed in the material to be dispensed.

One of skill will recognize that the functional relationships derived for the embodiments of FIGS. 1-2 will be tailored to the specific geometry, propellant pressures, size, pump characteristics, etc. of the device 21 under consideration. Additionally, the functional relationship will be specific to a particular material under consideration. If the rheology or material properties should change, the functional relationship may be adjusted accordingly. Additionally, the functional relationship may be tailored to each specific magent/Hall effect sensor 40 combination, as each component may have its own unique characteristics and to account for any variations in positioning such components on the device 21.

The embodiments shown in FIGS. 1-2 illustrate a magnet 42 incorporated into and disposed beneath the trigger 23. This provided the advantage that the entire measurement may be conducted invisible to the user. Particularly, the magnet 42 and Hall effect sensor 40 may not be visible to the user during ordinary intended use. The measuring system may be lightweight and small enough that a user may not notice and change the ordinary dispensing habits. Of course, one of skill will recognize the invention is not so limited. The illustrated positions of the magnet 42 and Hall effect sensor 40 may be reversed. Either or both components may be placed in different positions on the device 21, so long as the relative proximity therebetween, and hence a signal, can be detected in response to dispensing of materials from the reservoir.

Figure 3:
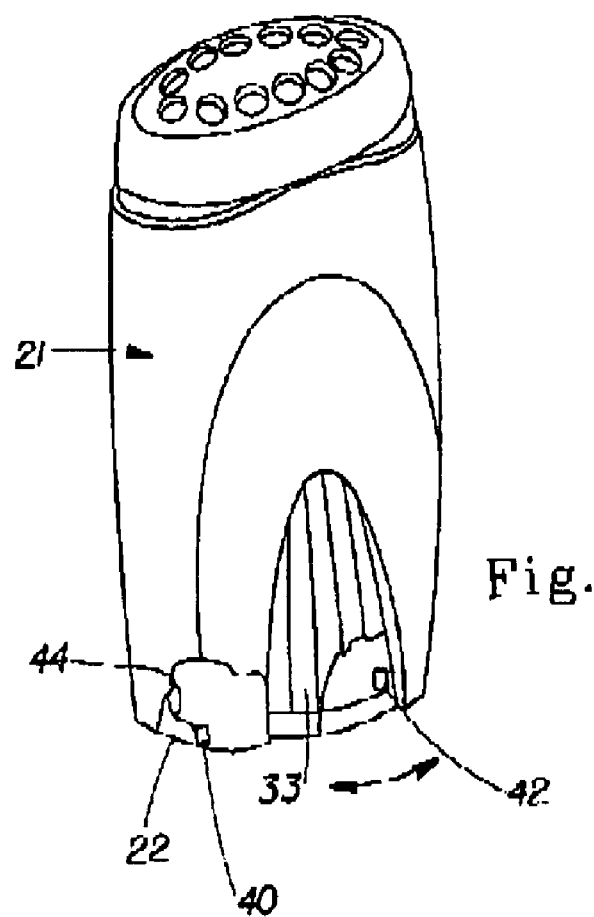
FIG. 3 is a perspective view of a screw thread/piston delivery device according to the present invention, shown partially in cutaway.

Referring to FIG. 3, the invention may be used with a screw thread device 21 used to drive a piston, as is common with antiperspirant/deodorants. The piston is driven axially along a screw. The screw has a longitudinal axis coincident the center of the screw and parallel to the dispensing direction. Relative rotation between the screw and a threaded nut advances the piston in the longitudinal direction.

Longitudinal advance of the piston may dispense the material contained in the reservoir of this device 21 by extrusion through one or more dispensing orifices. Such dispensing may be accomplished by rotating the screw/nut about the longitudinal axis. Rotation of the screw may occur through manually grasping a dial 33 disposed external to the device 21. The dial 33 is rotated perpendicular to and about the longitudinal axis.

A magnet 42 may be placed on one of the dial 33 and stationary components 22 the device 21. If desired, the magnet 42 may be annularly shaped, circumscribe the longitudinal axis and/or be disposed perpendicular thereto. Alternatively, a single magnet 42 disposed radially outboard of the dial 33 may provide a more distinct change in signal strength as it advances towards and away from the Hall effect sensor 40. Rotation of the magnet 42 with the dial 33, or Hall effect sensor 40 if mounted on the dial 33, produces a signal which can be correlated to advance of the piston. Advance of the piston is then correlatable to the amount of material dispensed.

If desired, the device 21 may comprise and unequal number of magnets 42 and Hall effect sensors 44. This arrangement provides the advantages of redundancy, as may be helpful in a harsh operating environment or where additional resolution is desired for different portions of the operating range.

The foreging measurements are quantitative. However, the present invention may also be used with qualitative measurements.

For example, the present invention may also be used to measure opening of and access to storage bags (not shown), as are commonly used for storing food leftovers. Such food storage bags have a seal formed by a track having complementary engaging portions. One of the Hall effect sensor 40 and magnet 42 may be disposed on each side of the bag. Upon opening, a change in proximity therebetween may be noted and one will know the contents of the bag were accessed or additional materials were added to the bag. Thus, the present invention is usable with a reservoir having generally flaccid walls.

Likewise, the present invention may be used with a reservoir having rigid walls (not shown) as are commonly used to contain wipes, tissues, etc. For example, a generally parallelpideally shaped container having a lid may be utilized. The container may be upright, generally flat or of any desired shape/geometry. The container may have a lid which can be closed to seal the contents therein and opened to access the materials therein for dispensing, as illustrated by commonly assigned U.S. Pat. Nos. 4,979,613 and 5,516,001. The lid may be hinged, removable, etc. to reveal the orifice through which materials may be dispensed. A Hall effect sensor 40 and a magnet 42 may be placed on the lid and sealing surface, respectively or vice versa. A change in the proximity therebetween will be detected and indicate access to the materials in the reservoir, or restocking of the reservoir, has occurred.

Additionally, the device 21 of the present invention can be used to determine the opening and closing of shades used to cover openings, such as windows. Exemplary shades are opened and closed using a drawstring as shown by commonly assigned U.S. Pat. No. 6,640,867 B1.

One of skill will recognize the invention described and claimed herein may also be used to monitor habits of using household products. For example the magnet 42/Hall effect sensor 40 combination cited herein may be used for monitoring placement of a toilet seat, opening/closing of a refrigerator door, opening/closing of a medicine cabinet door, or other aspects of a daily routine.

The dimensions and values disclosed herein are not to be understood as being strictly limited to the exact numerical values recited. Instead, unless otherwise specified, each such dimension is intended to mean both the recited value and a functionally equivalent range surrounding that value.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A device for quantitatively measuring an amount of a material dispensed, said device comprising:
   a reservoir for holding a material therein;

a dispensing orifice for dispensing material contained in said reservoir therefrom;

a dispenser for dispensing the material from the reservoir through said orifice, said dispenser having an actuator movable relative to said reservoir;

a member which is stationary relative to said dispenser;

a Hall effect sensor disposed on one of said dispenser and said stationary member;

a magnet disposed on the other of said dispenser and said stationary member, whereby relative movement between said magnet and said Hall effect sensor produces a signal in response to said movement, said signal being correlatable to a quantity of material dispensed from said reservoir.

2. A device according to claim 1 further comprising an electronically stored functional relationship, said functional relationship indicating a quantity of a material dispensed from said reservoir, wherein said material is dispensable in indeterminate quantities.

3. A device according to claim 2 comprising an unequal number of magnets and
Hall effect sensors.

4. A device according to claim 2 wherein said functional relationship is maintained remote from said device.

5. A device according to claim 4 wherein neither said magnet nor said sensor is visible to a user dispensing the material.

6. A device according to claim 1 wherein said magnet is disposed on said movable actuator and said sensor is disposed on said stationary member.

7. A device according to claim 6 wherein said actuator comprises a dial rotatable about a longitudinal axis and said dispenser further comprises a piston movable in the longitudinal direction and being operatively associated with said dial, wherein said magnet circumscribes said longitudinal axis.

8. A device according to claim 6 wherein said magnet moves in a rectilinear path.

9. A device according to claim 8 wherein said dispenser comprises a manually operated pump and said actuator comprises a trigger operatively associated with said pump.

10. A device according to claim 8 wherein said dispenser comprises a positive pressure relative to the atmospheric pressure and which maintains the material to be dispensed under a positive pressure, and said actuator comprises a valve openable to release said pressurized material and operatively associated with the pressurized material, wherein said reservoir has a major axis parallel the longitudinal direction and said magnet moves in a direction substantially parallel said longitudinal direction.

11. A method for quantitatively measuring an amount of a material dispensed, said method device comprising the steps of:

dispensing an indeterminate quantity of material from a reservoir for holding a material therein through an orifice, by moving an actuator relative to said reservoir, and thereby causing a signal to be produced between a Hall effect sensor and a magnet in response to said movement, wherein said material is not dispensed in discrete, predetermined units; and correlating said movement to a quantity of material dispensed from said reservoir by movement of said actuator.

12. A method according to claim 11 further comprising the step of monitoring the time and date of dispensing the material.

* * * * *